United States Patent [19]

Pardee et al.

[11] Patent Number: 5,262,311
[45] Date of Patent: Nov. 16, 1993

[54] METHODS TO CLONE POLYA MRNA

[75] Inventors: Arthur B. Pardee, Brookline; Peng Liang, Watertown, both of Mass.

[73] Assignee: Dana-Farber Cancer Institute, Inc., Boston, Mass.

[21] Appl. No.: 850,343

[22] Filed: Mar. 11, 1992

[51] Int. Cl.[5] .......................... C12P 19/34; C12Q 1/68
[52] U.S. Cl. ......................................... 435/91.2; 435/6
[58] Field of Search ...................... 435/91, 6

[56] References Cited

U.S. PATENT DOCUMENTS 4,683,195  7/1987  Mullis et al. ........................... 435/6

OTHER PUBLICATIONS

Liang et al. Science 257:967–971 (1992).
Gilliland et al. in "PCR protocols: A guide to methods and application" pp. 60–69, 1990.
Freifelder, D. "Molecular Biology" pp. 402–404 1983.
Sambrook, et al., Molecular Cloning: A Laboratory Manual, Second Edition, Cold Spring Harbor Press, pp. 8.6–8.35 (1989).
Sargent, T. D., "Isolation of Differentially Expressed Genes", 1987, Methods in Enzymology, vol. 152, pp. 423-ff.
Lee, S. W., et al., "Positive Selection of Candidate Tumor-Suppressor Genes by Subtractive Hybridization", 1991, Proc. Natl. Acad. Sci. USA, vol. 88, pp. 2825–2829.
Walker, G. T., et al., "Isothermal In Vitro Amplification of DNA by a Restriction Enzyme/DNA Polymerase System", 1992, vol. 89, pp. 392–396.
Williams, J., et al., "DNA Polymorphisms Amplified by Arbitrary Primers are Useful as Genetic Markers", 1990, Nucleic Acids Research, vol. 18, pp. 6531–6535.

Primary Examiner—Margaret Parr
Assistant Examiner—Paul B. Tran
Attorney, Agent, or Firm—Choate, Hall & Stewart

[57] ABSTRACT

A method for isolating mRNAs as cDNAs employs a polymerase amplification method using at least two oligodeoxynucleotide primers, one being short with arbitrary sequence and another being either short with arbitrary sequence or being capable of hybridizing to the region near the mRNA polyA tail. The oligodeoxynucleotide that is capable of hybridizing to the region near the polyA tail is used as a primer for reverse transcription of the mRNA and the resultant cDNA is amplified with a polymerase using both oligodeoxynucleotides as a primer set.

18 Claims, 2 Drawing Sheets

```
          10         20         30         40         50         60
  CTTGATTGCC TCCTACAGCA GTTGCAGGCA CCTTTAGCTG TACCATGAAG TTCACAGTCC
     ‾15
          70         80         90        100        110        120
  GGGATTGTGA CCCTAATACT GGAGTTCCAG ATGAAGATGG ATATGATGAT GAATATGTGC
         130        140        150        160        170        180
  TGGAAGATCT TGAGGTAACT GTGTCTGATC ATATTCAGAA GATACTAAAA CCTAACTTCG
         190        200        210        220        230        240
  CTGCTGCCTG GGAAGAGGTG GGAGGAGCAG CTGCGACAGA GCGTCCTCTT CACAGAGGGG
         250        260
  TCCTGGGTGA AAAAAAAAAA
                     ‾16
```

METHODS TO CLONE POLYA MRNA

BACKGROUND OF THE INVENTION

This invention relates to methods of detecting and cloning of individual mRNAs.

The activities of genes in cells are reflected in the kinds and quantities of their mRNA and protein species. Gene expression is crucial for processes such as aging, development, differentiation, metabolite production, progression of the cell cycle, and infectious or genetic or other disease states. Identification of the expressed mRNAs will be valuable for the elucidation of their molecular mechanisms, and for applications to the above processes.

Mammalian cells contain approximately 15,000 different mRNA sequences, however, each mRNA sequence is present at a different frequency within the cell. Generally, mRNAs are expressed at one of three levels. A few "abundant" mRNAs are present at about 10,000 copies per cell, about 3,000-4,000 "intermediate" mRNAs are present at 300-500 copies per cell, and about 11,000 "low-abundance" or "rare" mRNAs are present at approximately 15 copies per cell. The numerous genes that are represented by intermediate and low frequencies of their mRNAs can be cloned by a variety of well established techniques (see for example Sambrook et al., 1989, Molecular Cloning: A Laboratory Manual, Second Edition, Cold Spring Harbor Press, pp. 8.6–8.35).

If some knowledge of the gene sequence or protein is had, several direct cloning methods are available. However, if the identity of the desired gene is unknown one must be able to select or enrich for the desired gene product in order to identify the "unknown" gene without expending large amounts of time and resources.

The identification of unknown genes can often involve the use of subtractive or differential hybridization techniques. Subtractive hybridization techniques rely upon the use of very closely related cell populations, such that differences in gene expression will primarily represent the gene(s) of interest. A key element of the subtractive hybridization technique is the construction of a comprehensive complementary DNA ("cDNA") library.

The construction of a comprehensive cDNA library is now a fairly routine procedure. PolyA mRNA is prepared from the desired cells and the first strand of the cDNA is synthesized using RNA-dependent DNA polymerase ("reverse transcriptase") and an oligodeoxynucleotide primer of 12 to 18 thymidine residues. The second strand of the cDNA is synthesized by one of several methods, the more efficient of which are commonly known as "replacement synthesis" and "primed synthesis".

Replacement synthesis involves the use of ribonuclease H ("RNAase H"), which cleaves the phosphodiester backbone of RNA that is in a RNA:DNA hybrid leaving a 3' hydroxyl and a 5' phosphate, to produce nicks and gaps in the mRNA strand, creating a series of RNA primers that are used by E. coli DNA polymerase I, or its "Klenow" fragment, to synthesize the second strand of the cDNA. This reaction is very efficient; however, the cDNAs produced most often lack the 5' terminus of the mRNA sequence.

Primed synthesis to generate the second cDNA strand is a general name for several methods which are more difficult than replacement synthesis yet clone the 5' terminal sequences with high efficiency. In general, after the synthesis of the first cDNA strand, the 3' end of the cDNA strand is extended with terminal transferase, an enzyme which adds a homopolymeric "tail" of deoxynucleotides, most commonly deoxycytidylate. This tail is then hybridized to a primer of oligodeoxyguanidylate or a synthetic fragment of DNA with an deoxyguanidylate tail and the second strand of the cDNA is synthesized using a DNA-dependent DNA polymerase.

The primed synthesis method is effective, but the method is laborious, and all resultant cDNA clones have a tract of deoxyguanidylate immediately upstream of the mRNA sequence. This deoxyguanidylate tract can interfere with transcription of the DNA in vitro or in vivo and can interfere with the sequencing of the mRNA sequence by the Sanger dideoxynucleotide sequencing method.

Once both cDNA strands have been synthesized, the cDNA library is constructed by cloning the cDNAs into an appropriate plasmid or viral vector. In practice this can be done by directly ligating the blunt ends of the cDNAs into a vector which has been digested by a restriction endonuclease to produce blunt ends. Blunt end ligations are very inefficient, however, and this is not a common method of choice. A generally used method involves adding synthetic linkers or adapters containing restriction endonuclease recognition sequences to the ends of the cDNAs. The cDNAs can then be cloned into the desired vector at a greater efficiency.

Once a comprehensive cDNA library is constructed from a cell line, desired genes can be identified with the assistance of subtractive hybridization (see for example Sargent T. D., 1987, Meth. Enzymol., Vol. 152, pp. 423–432; Lee et al., 1991, Proc. Natl. Acad. Sci., USA, Vol. 88, pp. 2825–2830). A general method for subtractive hybridization is as follows. The complementary strand of the cDNA is synthesized and radiolabelled. This single strand of cDNA can be made from polyA mRNA or from the existing cDNA library. The radiolabelled cDNA is hybridized to a large excess of mRNA from a closely related cell population. After hybridization the cDNA:mRNA hybrids are removed from the solution by chromatography on a hydroxylapatite column. The remaining "subtracted" radiolabelled cDNA can then be used to screen a cDNA or genomic DNA library of the same cell population.

Subtractive hybridization removes the majority of the genes expressed in both cell populations and thus enriches for genes which are present only in the desired cell population. However, if the expression of a particular mRNA sequence is only a few times more abundant in the desired cell population than the subtractive population it may not be possible to isolate the gene by subtractive hybridization.

SUMMARY OF THE INVENTION

We have discovered that mRNAs can be identified and isolated as cDNAs using a polymerase amplification method that employs two oligodeoxynucleotide primers, one being short with arbitrary sequence and another being either short with arbitrary sequence or being capable of hybridizing to the region near the polyA tail. The oligodeoxynucleotide that is capable of hybridizing to the region near the polyA tail is used as a primer for reverse transcription of the mRNA and the resultant cDNA is amplified with a polymerase using both oligodeoxynucleotides as a primer set.

Using this method with different pairs of the alterable primers, virtually any or all of the mRNAs from any cell type or any stage of the cell cycle, including very low abundance mRNAs, can be identified and isolated. Additionally a comparison of the mRNAs from closely related cells, which may be for example at different stages of development or different stages of the cell cycle, can show which of the mRNAs are constitutively expressed and which are differentially expressed, and their respective frequencies of expression.

The "arbitrary" sequence of an oligodeoxynucleotide as used herein is defined as being based upon or subject to individual judgement or discretion. In some instances, the arbitrary sequence can be entirely random or partly random for one or more bases. In other instances the arbitrary sequence can be selected to contain a specific ratio of each deoxynucleotide, or can be selected to contain, or not to contain, a recognition site for specific restriction endonuclease, or can be selected to either contain or not contain sequence from a known mRNA.

The "preferred length" of an oligodeoxynucleotide, as used herein, is determined from the desired specificity of annealling and the number of oligodeoxynucleotides having the desired specificity that are required to hybridize to the mRNAs in a cell. An oligodeoxynucleotide of 20 nucleotides is more specific than an oligodeoxynucleotide of 10 nucleotides; however, addition of each random nucleotide to an oligodeoxynucleotide increases by four the number of oligodeoxynucleotides required in order to hybridize to every mRNA in a cell.

In one aspect, in general, the invention features a method for identifying and isolating mRNAs by priming a preparation of mRNA for reverse transcription with an oligodeoxynucleotide that contains a sequence capable of hybridizing to the region near the polyA tail of mRNA ("3' oligodeoxynucleotide"), and amplifying the cDNA by a polymerase amplification method using the 3' oligodeoxynucleotide and the short arbitrary sequence oligodeoxynucleotide ("5' oligodeoxynucleotide") as a primer set.

In preferred embodiments, the 3' oligodeoxynucleotide contains at least 1 nucleotide at the 3' end of the oligodeoxynucleotide that can hybridize to an mRNA sequence that is immediately upstream of the polyA tail, and contains at least 11 nucleotides at the 5' end that will hybridize to the polyA tail. The entire 3' oligodeoxynucleotide is preferably at least 13 nucleotides in length, and can be up to 20 nucleotides in length.

Most preferably the 3' oligodeoxynucleotide contains 2 nucleotides at the 3' end of the oligodeoxynucleotide that can hybridize to an mRNA sequence that is immediately upstream of the polyA tail. Preferably, the 2 polyA-non-complementary nucleotides are of the sequence VN, where V is deoxyadenylate ("dA"), deoxyguanylate ("dG"), or deoxycytidylate ("dC"), and N, the 3' terminal nucleotide, is dA, dG, dC, or deoxythymidylate ("dT"). The use of 2 nucleotides can provide accurate positioning of the 3' oligodeoxynucleotide at the junction between the mRNA and its polyA tail, as the properly aligned oligodeoxynucleotide:mRNA hybrids are more stable than improperly aligned hybrids, and thus the properly aligned hybrids will form and remain hybridized at higher temperatures. In preferred applications, the mRNA sample will be divided into at least twelve aliquots and one of the 12 possible VN sequences of the 3' oligodeoxynucleotide will be used in each reaction to prime the reverse transcription of the mRNA. The use of an oligodeoxynucleotide with a single sequence will reduce the number of mRNAs to be analyzed in each sample by binding to a subset of the mRNAs, statistically 1/12th, thus simplifying the identification of the mRNAs in each sample.

In some embodiments, the 3' end of the 3' oligodeoxynucleotide can have 1 nucleotide that can hybridize to an mRNA sequence that is immediately upstream of the polyA tail, and 12 nucleotides at the 5' end that will hybridize to the polyA tail. The use of a single non-polyA-complementary oligodeoxynucleotide would decrease the number of oligodeoxynucleotides that are required to identify every mRNA to 3, however, the use of a single nucleotide to position the annealing of primer to the junction of the mRNA sequence and the polyA tail may result in a significant loss of specificity of the annealing and 2 non-polyA-complementary nucleotides are preferred.

In some embodiments, the 3' end of the 3' oligodeoxynucleotide can have 3 or more nucleotides that can hybridize to an mRNA sequence that is immediately upstream of the polyA tail. The addition of each nucleotide to the 3' end will further increase the stability of properly aligned hybrids, and the sequence to hybridize to the polyA tail can be decreased by one nucleotide for each additional non-polyA-complementary nucleotide added. The use of such a 3' oligodeoxynucleotide may not be practical for rapid screening of the mRNAs contained within a given cell line, as the use of a 3' oligodeoxynucleotide with more than 2 nucleotides that hybridize to the mRNA immediately upstream of the polyA tail significantly increases the number of oligonucleotides required to identify every mRNA. For instance, the 3' sequence VNN would require the use of 48 separate 3' oligodeoxynucleotides in order to bind to every mRNA, and would significantly increase the number of reactions required to screen the mRNA from a given cell line. The use of oligodeoxynucleotides with a single random nucleotide in one position as a group of four can circumvent the problem of needing to set up 48 separate reactions in order to identify every mRNA. However as the non-polyA-complementary sequence became longer, it would quickly become necessary to increase the number of reactions required to identify every mRNA.

In other preferred embodiments, the 3' oligodeoxynucleotide contains nucleotides that will hybridize to the polyadenylation signal sequence and at least 4 nucleotides that are positioned 5', or 3', or both of the polyadenylation signal sequence; the entire 3' oligodeoxynucleotide is preferably at least 10 nucleotides in length, and can be up to 20 nucleotides in length. In one preferred embodiment the sequence NNTTTATTNN, SEQ ID NO. 2, be chosen such that the sequence is GCTTTATTNC, SEQ ID NO: 3, and the four resultant oligodeoxynucleotides are used together in a single reaction for the priming of the mRNA for reverse transcription.

In other embodiments the 3' oligodeoxynucleotide can be of arbitrary sequence. An arbitrary sequence 3' oligodeoxynucleotide is preferably at least 9 nucleotides in length. Preferably the 3' oligodeoxynucleotide is at most 13 nucleotides in length and can be up to 20 nucleotides in length.

In preferred embodiments the 5' short arbitrary sequence oligodeoxynucleotide is at least 9 nucleotides in length. Preferably the 5' oligodeoxynucleotide is at most 13 nucleotides in length and can be up to 20 nucleotides in length.

In some preferred embodiments the amplified cDNAs are separated and then the desired cDNAs are reamplified using a polymerase amplification reaction and the 5' and 3' oligodeoxynucleotides.

In preferred embodiments a set of 5' and 3' oligodeoxynucleotide primers can be used, consisting of more than one of each primer. In some embodiments more than one of the 3' primer will be included in the reverse transcription reaction and more than one each of the 5' and the 3' primers will be included in the amplification reactions. The use of more than one of each primer will increase the number of mRNAs identified in each reaction, and the total number of primers to be used will be determined based upon the desired method of separating the cDNAs such that it remains possible to fully isolate each individual cDNA. In preferred embodiments a few hundred cDNAs can be isolated and identified using denaturing polyacrylamide gel electrophoresis.

The method according to the invention is a significant advance over current cloning techniques that utilize subtractive hybridization. In one aspect, the method according to the invention enables the genes which are altered in their frequency of expression, as well as of mRNAs which are constitutively and differentially expressed, to be identified by simple visual inspection and isolated. In another aspect the method according to the invention provides specific oligodeoxynucleotide primers for amplification of the desired mRNA as cDNA and makes unnecessary an intermediary step of adding a homopolymeric tail to the first cDNA strand for priming of the second cDNA strand and thereby avoiding any interference from the homopolymeric tail with subsequent analysis of the isolated gene and its product. In another aspect the method according to the invention allows the cloning and sequencing of selected mRNAs, so that the investigator may determine the relative desirability of the gene prior to screening a comprehensive cDNA library for the full length gene product.

DESCRIPTION OF THE PREFERRED EMBODIMENTS

Drawings

General Description, Development of the Method

By way of illustration a description of examples of the method of the invention follows, with a description by way of guidance of how the particular illustrative examples were developed.

It is important for operation of the method that the length of the oligonucleotides be appropriate for specific hybridization to mRNA. In order to obtain specific hybridization, whether for conventional cloning methods or PCR, oligodeoxynucleotides are usually chosen to be 20 or more nucleotides in length. The use of long oligodeoxynucleotides in this instance would decrease the number of mRNAs identified during each trial and would greatly increase the number of oligodeoxynucleotides required to identify every mRNA. Recently, it was demonstrated that 9-10 nucleotide primers can be used for DNA polymorphism analysis by PCR (Williams et al., 1991, *Nuc. Acids Res.*, Vol. 18, pp. 6531-6535).

The plasmid containing the cloned murine thymidine kinase gene ("TK cDNA plasmid") was used as a model template to determine the required lengths of oligodeoxynucleotides for specific hybridization to a mRNA, and for the production of specific PCR products. The oligodeoxynucleotide primer chosen to hybridize internally in the mRNA was varied between 6 and 13 nucleotides in length, and the oligodeoxynucleotide primer chosen to hybridize at the upstream end of the polyA tail was varied between 7 and 14 nucleotides in length. After numerous trials with different sets and lengths of primers, it was determined that the annealing temperature of 42° C. is optimal for product specificity and the internally hybridizing oligodeoxynucleotide should be at least 9 nucleotides in length and a oligodeoxynucleotide that is at least 13 nucleotides in length is required to bind to the upstream end of the polyA tail.

Figure 1:
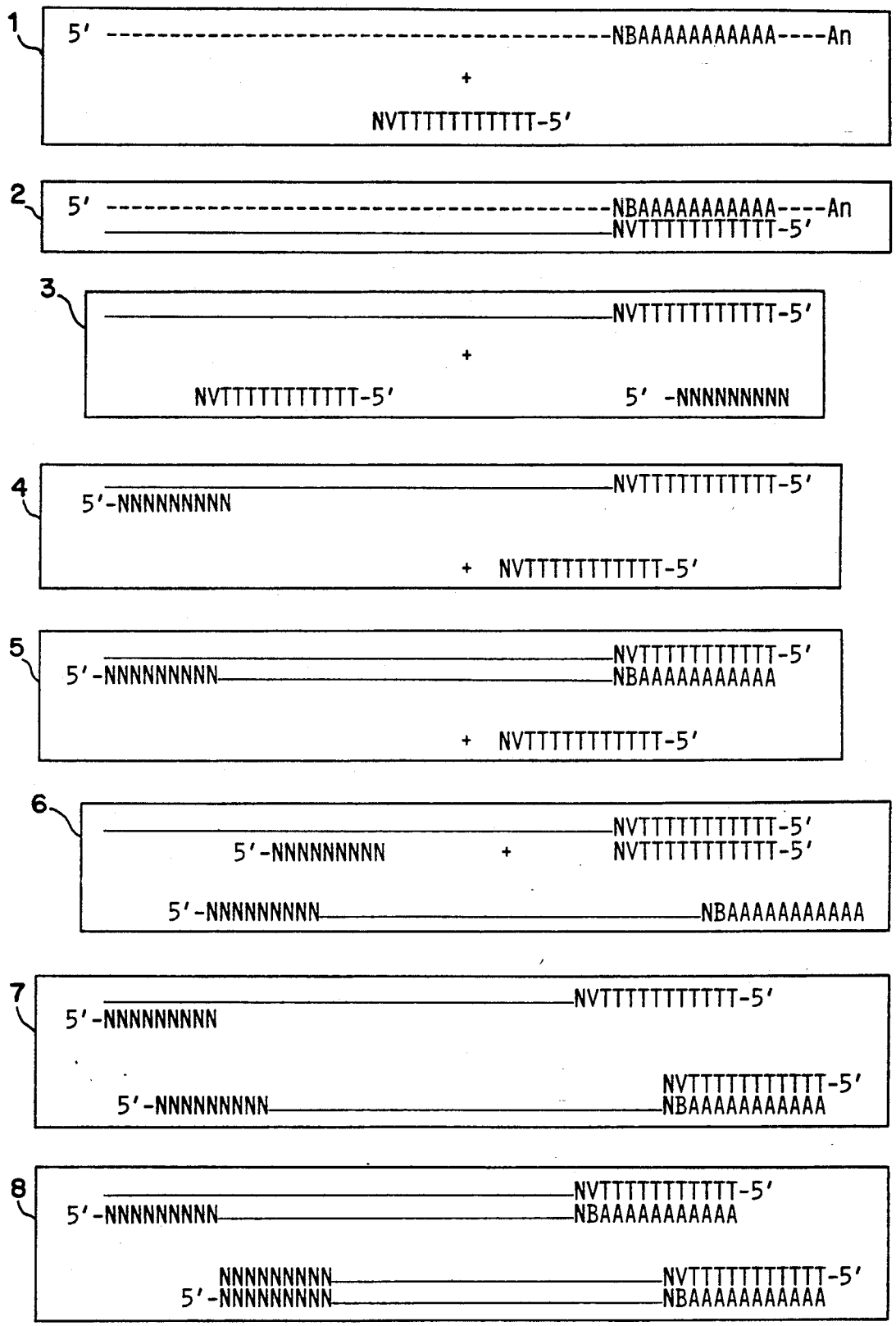
FIG. 1 is a schematic representation of the method according to the invention.

With reference now to FIG. 1, the method according to the invention is depicted schematically. The mRNAs are mixed with the 3' oligodeoxynucleotide, for example TTTTTTTTTTT VN ("$T_{11}VN$"), SEQ ID NO: 4,1, and reverse transcribed 2 to make the first cDNA strand. The cDNA is added to the 5' arbitrary sequence oligodeoxynucleotide, the 3' oligodeoxynucleotide and the polymerase in the standard buffer with the appropriate concentrations of nucleotides and the components are heated to 94° C. to denature the mRNA:cDNA hybrid 3, the temperature is reduced to 42° C. to allow the arbitrary sequence oligodeoxynucleotide to anneal 4, and then the temperature is increased to 72° C. to allow the polymerase to extend the 5' oligodeoxynucleotide 5. The cycling of the temperature is then repeated 6, 7, 8, to begin the amplification of the sequences which are hybridized by the two oligodeoxynucleotide primers. The temperature is cycled until the desired number of copies of each sequence have been made.

The following examples of the method of the invention are presented for illustrative purposes only. As will be appreciated, the method according to the invention can be used for the isolation of polyA mRNA from any source and can be used to isolate genes expressed either differentially or constitutively at any level, from rare to abundant.

EXAMPLE 1

Experimentation with the conditions required for accurate and reproducible results by PCR were conducted with the TK cDNA plasmid and a single set of oligodeoxynucleotide primers; the sequence TTTTTTTTTTTCA, ("$T_{11}CA$"), SEQ ID No: 5, was chosen to hybridize to the upstream end of the polyA tail and the sequence CTTGATTGCC ("Ltk3"), SEQ ID No:6, was chosen to hybridize 288 base pairs ("bp") upstream of the polyA tail. The expected fragment size using these two primers is 299 bp.

PCR was conducted under standard buffer conditions well known in the art with 10 ng TK cDNA plasmid (buffer and polymerase are available from Perkin Elmer-Cetus). The standard conditions were altered in that the primers were used at concentrations of 2.5 $\mu M$ $T_{11}CA$, 0.5 $\mu M$ Ltk3, instead of 1 $\mu M$ of each primer. The concentration of the nucleotides ("dNTPs") was also varied over a 100 fold range, from the standard 200 $\mu M$ to 2 $\mu M$. The PCR parameters were 40 cycles of a denaturing step for 30 seconds at 94° C., an annealing step for 1 minute at 42° C., and an extension step for 30 seconds at 72° C. Significant amounts of non-specific PCR products were observed when the dNTP concentration was 200 μM, concentrations of dNTPs at or below 20 μM yielded specifically amplified PCR products. The specificity of the PCR products was verified by restriction endonuclease digest of the amplified DNA, which yielded the expected sizes of restriction fragments. In some instances it was found that the use of up to 5 fold more of the 3' oligodeoxynucleotide than the 5' oligodeoxynucleotide also functioned to increase the specificity of the product. Lowering the dNTP concentration to 2 μM allowed the labelling of the PCR products to a high specific activity with [α−$^{35}$S] dATP, 0.5 μM [α−$^{35}$S] dATP (Sp. Act. 1200 Ci/mmol), which is necessary for distinguishing the PCR products when resolved by high resolution denaturing polyacrylamide gel electrophoresis, in this case a DNA sequencing gel.

EXAMPLE 2

The PCR method of amplification with short oligodeoxynucleotide primers was then used to detect a subset of mRNAs in mammalian cells. Total RNAs and mRNAs were prepared from mouse fibroblasts cells which were either growing normally, "cycling", or serum starved, "quiescent". The RNAs and mRNAs were reverse transcribed with $T_{11}CA$ as the primer. The $T_{11}CA$ primer was annealed to the mRNA by heating the mRNA and primer together to 65° C. and allowing the mixture to gradually cool to 35° C. The reverse transcription reaction was carried out with Moloney murine leukemia virus reverse transcriptase at 35° C. The resultant cDNAs were amplified by PCR in the presence of $T_{11}CA$ and Ltk3, as described in Example 1, using 2 μM dNTPs. The use of the $T_{11}CA$ and Ltk3 primers allowed the TK mRNA to be used as an internal control for differential expression of a rare mRNA transcript; TK mRNA is present at approximately 30 copies per cell. The DNA sequencing gel revealed 50 to 100 amplified mRNAs in the size range which is optimal for further analysis, between 100 to 500 nucleotides. The patterns of the mRNA species observed in cycling and quiescent cells were very similar as expected, though some differences were apparent. Notably, the TK gene mRNA, which is expressed during G1 and S phase, was found only in the RNA preparations from cycling cells, as expected, thus demonstrating the ability of this method to separate and isolate rare mRNA species such as TK.

EXAMPLE 3

The expression of mRNAs in normal and tumorigenic mouse fibroblast cells was also compared using the $T_{11}CA$ and Ltk3 primers for the PCR amplification. The mRNA was reverse transcribed using $T_{11}CA$ as the primer and the resultant cDNA was amplified by PCR using 2 μM dNTPs and the PCR parameters described above. The PCR products were separated on a DNA sequencing gel. The TK mRNA was present at the same level in both the normal and tumorigenic mRNA preparations, as expected, and provided a good internal control to demonstrate the representation of rare mRNA species. Several other bands were present in one preparation and not in the other, with a few bands present in only the mRNA from normal cells and a few bands present only in the mRNA from the tumorigenic cells; and some bands were expressed to different levels in the normal and tumorigenic cells. Thus, the method according to the invention can be used to identify genes which are normally continuously expressed (constitutive), and differentially expressed, suppressed, or otherwise altered in their level of expression.

CLONING OF THE IDENTIFIED mRNA

Three cDNAs that are, the TK cDNA, one cDNA expressed only in normal cells ("N1"), and one cDNA expressed only in tumorigenic cells ("T1"), were recovered from the DNA sequencing gel by electroelution, ethanol precipitated to remove the urea and other contaminants, and reamplified by PCR, in two consecutive PCR amplifications of 40 cycles each, with the primers $T_{11}CA$ and Ltk3 in the presence of 20 μM dNTPs to achieve optimal yield without compromising the specificity. The reamplified PCR products were confirmed to have the appropriate sizes and primer dependencies as an additional control the reamplified TK cDNA was digested with two separate restriction endonucleases and the digestion products were also confirmed to be of the correct size.

Figures 2, 3:
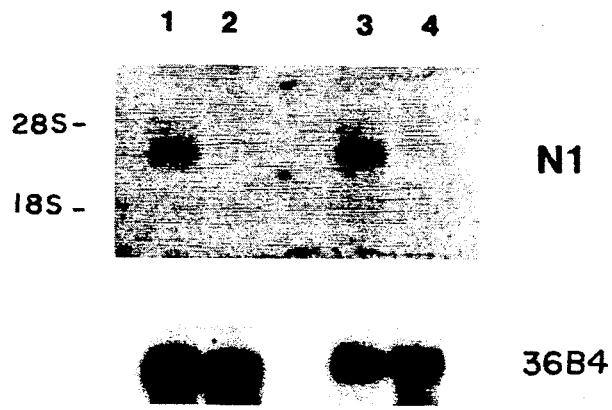
FIG. 2 is the sequence of the 3' end of the N1 gene SEQ ID NO: 1, from normal mouse fibroblast cells (A31).
FIG. 3 is the Northern blot of the N1 sequence on total cellular RNA from normal and tumorigenic mouse fibroblast cells.

The reamplified N1 was cloned with the TA cloning system, Invitrogen Inc., into the plasmid pCR1000 and sequenced. With reference now to FIG. 2, the nucleotide sequence clearly shows the N1 fragment to be flanked by the underlined Ltk3 primer 15 at the 5' end and the underlined $T_{11}CA$ primer 16 at the 3' end as expected.

A Northern analysis of total cellular RNA using a radiolabelled N1 probe reconfirmed that the N1 mRNA was only present in the normal mouse fibroblast cells, and not in the tumorigenic mouse fibroblast cells. With reference now to FIG. 3, the probe used to detect the mRNA is labelled to the right of the figure, and the size of the N1 mRNA can be estimated from the 28S and 18S markers depicted to the left of the figure. The N1 mRNA is present at low abundance in both exponentially growing and quiescent normal cells, lanes 1 and 3, and is absent from both exponentially growing or quiescent tumorigenic cells, lanes 2 and 4. As a control, the same Northern blot was reprobed with a radiolabelled probe for 36B4, a gene that is expressed in both normal and tumorigenic cells, to demonstrate that equal amounts of mRNA, lanes 1–4, were present on the Northern blot.

USE

The method according to the invention can be used to identify, isolate and clone mRNAs from any number of sources. The method provides for the identification of desirable mRNAs by simple visual inspection after separation, and can be used for investigative research, industrial and medical applications.

For instance, the reamplified cDNAs can be sequenced, or used to screen a DNA library in order to obtain the full length gene. Once the sequence of the cDNA is known, amino acid peptides can be made from the translated protein sequence and used to raise antibodies. These antibodies can be used for further research of the gene product and its function, or can be applied to medical diagnosis and prognosis. The reamplified cDNAs can be cloned into an appropriate vector for further propagation, or cloned into an appropriate expression vector in order to be expressed, either in vitro or in vivo. The cDNAs which have been cloned into expression vectors can be used in industrial situations for overproduction of the protein product. In other applications the reamplified cDNAs or their respective clones will be used as probes for in situ hybridization. Such probes can also be used for the diagnosis or prognosis of disease.

OTHER EMBODIMENTS

Other embodiments are within the following claims.

The length of the oligonucleotides can be varied dependent upon the annealing temperature chosen. In the preferred embodiments the temperature was chosen to be 42° C. and the oligonucleotide primers were chosen to be at least 9 nucleotides in length. If the annealing temperature were decreased to 35° C. then the oligonucleotide lengths can be decreased to at least 6 nucleotides in length.

The cDNA could be radiolabelled with radioactive nucleotides other than $^{35}S$, such as $^{32}P$ and $^{33}P$. When desired, non-radioactive imaging methods can also be applied to the method according to the invention.

The amplification of the cDNA could be accomplished by a temperature cycling polymerase chain reaction, as was described, using a heat stable DNA polymerase for the repetitive copying of the cDNA while cycling the temperature for continuous rounds of denaturation, annealing and extension. Or the amplification could be accomplished by an isothermal DNA amplification method (Walker et al., 1992, *Proc. Natl. Acad. Sci.*, Vol. 89, pp. 392-396). The isothermal amplification method would be adapted to use for amplifying cDNA by including an appropriate restriction endonuclease sequence, one that will be nicked at hemiphosphorothioate recognition sites and whose recognition site can be regenerated during synthesis with $\alpha^{35}S$ labelled dNTPs.

We claim:

1. A non-specific cloning method for isolating in a nucleic acid sample a DNA complementary to a mRNA, comprising
   contacting the mRNA with a first oligodeoxynucleotide primer which hybridizes to a portion of the polyadenosine (polyA) tail of said mRNA and at least one non-polyA nucleotide immediately upstream of said portion,
   reverse transcribing the mRNA using a reverse transciptase and said first primer to produce a first DNA strand complementary to said mRNA,
   contacting said first DNA strand with a second oligodeoxynucleotide primer under conditions in which said second primer hybridizes with said first DNA strand,
   extending said second primer using a DNA polymerase to produce a second DNA strand complementary said first DNA strand, and
   amplifying said first and second DNA strands using a DNA polymerase and said first and second primers to clone the DNA.

2. The method of claim 1 wherein said first primer hybridizes to said portion and at least two nucleotides immediately upstream of said portion.

3. The method of claim 1 wherein said first primer includes a polyA-complementary region comprising at least 11 nucleotides and, immediately downstream from said polyA-complementary region, a non-polyA-complementary region comprising at least one nucleotide.

4. The method of claim 3 wherein said polyA-complementary region comprises at least 11 contiguous thymidines.

5. The method of claim 3 wherein said non-polyA-complementary region comprises at least 2 contiguous nucleotides.

6. The method of claim 4 or 5 wherein said non-polyA-complementary region comprises 3'-NV, wherein V is one of deoxyadenosine, deoxycytidine or deoxyguanosine, and N is one of deoxyadenosine, deoxythymidine, deoxycytidine or deoxyguanosine.

7. The method of claim 3 wherein said first primer comprises at least 13 nucleotides.

8. A non-specific cloning method for isolating in a nucleic acid sample a DNA complementary to a mRNA, comprising contacting the mRNA with a first oligodeoxynucleotide primer which hybridizes with the mRNA at a site that includes the mRNA's polyA signal sequence, reverse transcribing the mRNA using a reverse transcriptase and said first primer, to produce a first DNA strand complementary to said mRNA, contacting said first DNA strand with a second oligodeoxynucleotide primer under conditions in which said second primer hybridizes with said first DNA strand;

extending said second primer using a DNA polymerase to produce a second DNA strand complementary to said first DNA strand; and amplifying said first and second DNA strands using a DNA polymerase and said first and second primers to clone the DNA.

9. The method of claim 8 wherein said first primer comprises at least 6 nucleotides.

10. The method of claim 8 wherein said first primer comprises at least 9 nucleotides.

11. The method of claim 1 or 8 wherein said second primer comprises at least 6 nucleotides.

12. The method of claim 1 or 8 wherein said second primer comprises at least 9 nucleotides.

13. The method of claim 11 or 12 wherein the nucleotide sequence of said second primer is selected at random.

14. The method of any of claims 7–12 wherein the nucleotide sequence of said first or second primer includes a selected arbitrary sequence.

15. The method of any of claims 9–12 wherein the nucleotide sequence of said first or said second primer includes deoxycytidine, deoxyguanosine, deoxythymidine and deoxyadenosine.

16. The method of any of claims (–12 wherein the nucleotide sequence of said first or second primer contains a restriction endonuclease recognition sequence.

17. The method of any of claims 9–12 wherein the nucleotide sequence of said first and second primer includes a sequence identical to a sequence contained within a mRNA of which the nucleotide sequence is known.

18. The method of claim 1 or 8 wherein at least one of said first or second primers comprises a plurality of oligodeoxynucleotides.

* * * * *

UNITED STATES PATENT AND TRADEMARK OFFICE
CERTIFICATE OF CORRECTION

PATENT NO. : 5,262,311
DATED : November 16, 1993
INVENTOR(S) : Arthur B. Pardee, et al It is certified that error appears in the above-indentified patent and that said Letters Patent is hereby corrected as shown below:

Column 14, line 19:  please delete "(-12 and insert therefor -- 9-12--.

Signed and Sealed this

Twenty-fourth Day of May, 1994

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,262,311
DATED : November 16, 1993
INVENTOR(S) : Arthur B. Pardee, et. al.

It is certified that error appears in the above-indentified patent and that said Letters Patent is hereby corrected as shown below:

Column 4, line 56, before "be", insert "can";

Column 14, line 23, delete "and" and insert therefor -- or --.

Signed and Sealed this

Twenty-sixth Day of September, 1995

Attest:

BRUCE LEHMAN

Attesting Officer    Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 260 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( G ) CELL TYPE: Fibroblast
( H ) CELL LINE: A31

( x i ) SEQUENCE DESCRIPTION: SEQ ID NO:1:

```
CTTGATTGCC  TCCTACAGCA  GTTGCAGGCA  CCTTTAGCTG  TACCATGAAG  TTCACAGTCC    60
GGGATTGTGA  CCCTAATACT  GGAGTTCCAG  ATGAAGATGG  ATATGATGAT  GAATATGTGC   120
TGGAAGATCT  TGAGGTAACT  GTGTCTGATC  ATATTCAGAA  GATACTAAAA  CCTAACTTCG   180
CTGCTGCCTG  GGAAGAGGTG  GGAGGAGCAG  CTGCGACAGA  GCGTCCTCTT  CACAGAGGGG   240
TCCTGGGTGA  AAAAAAAAA                                                    260
```

( 2 ) INFORMATION FOR SEQ ID NO:2:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:2:

```
NNTTTATTNN                                                                10
```

( 2 ) INFORMATION FOR SEQ ID NO:3:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:3:

GCTTTATTNC  10

( 2 ) INFORMATION FOR SEQ ID NO:4:

( i ) SEQUENCE CHARACTERISTICS:
            ( A ) LENGTH: 13 base pairs
            ( B ) TYPE: nucleic acid
            ( C ) STRANDEDNESS: single
            ( D ) TOPOLOGY: linear ( i i i ) HYPOTHETICAL: NO ( i v ) ANTI-SENSE: NO ( x i ) SEQUENCE DESCRIPTION: SEQ ID NO:4:

TTTTTTTTTT TVN  13

( 2 ) INFORMATION FOR SEQ ID NO:5:

( i ) SEQUENCE CHARACTERISTICS:
            ( A ) LENGTH: 13 base pairs
            ( B ) TYPE: nucleic acid
            ( C ) STRANDEDNESS: single
            ( D ) TOPOLOGY: linear ( i i i ) HYPOTHETICAL: NO ( i v ) ANTI-SENSE: NO ( x i ) SEQUENCE DESCRIPTION: SEQ ID NO:5:

TTTTTTTTTT TCA  13

( 2 ) INFORMATION FOR SEQ ID NO:6:

( i ) SEQUENCE CHARACTERISTICS:
            ( A ) LENGTH: 10 base pairs
            ( B ) TYPE: nucleic acid
            ( C ) STRANDEDNESS: single
            ( D ) TOPOLOGY: linear ( i i i ) HYPOTHETICAL: NO ( i v ) ANTI-SENSE: NO ( x i ) SEQUENCE DESCRIPTION: SEQ ID NO:6:

GTTGATTGCC  10